United States Patent [19]
Young et al.

[11] Patent Number: 6,004,932
[45] Date of Patent: Dec. 21, 1999

[54] USE OF GLUCAGON AS A METABOLIC CONDITIONER FOR DAIRY COWS AND OTHER RUMINANTS

[75] Inventors: Jerry W. Young; Donald C. Beitz, both of Ames, Iowa; Arnold R. Hippen, Flandreau, S. Dak.

[73] Assignee: Iowa State University Research Foundation, Inc., Ames, Iowa

[21] Appl. No.: 09/035,485

[22] Filed: Mar. 5, 1998

Related U.S. Application Data

[60] Provisional application No. 60/040,647, Mar. 6, 1997.

[51] Int. Cl.$^6$ .......................... A61K 38/00; A61K 38/26
[52] U.S. Cl. ........................... 514/12; 530/308; 530/324
[58] Field of Search ............................. 514/12; 530/308, 530/324

[56] References Cited

U.S. PATENT DOCUMENTS

| | | | |
|---|---|---|---|
| 4,369,172 | 1/1983 | Schor et al. | 424/19 |
| 5,143,902 | 9/1992 | Merrifield et al. | 514/12 |
| 5,597,797 | 1/1997 | Clark | 514/12 |

OTHER PUBLICATIONS

Brockman, R.P., "Roles for Insulin and Glucagon in the Development of Ruminant Ketosis—A Review" Can. Vet. J., 1976, 20, 121–126.
Wright, et al., "Glucagon (1–6) binds to Glucagon Receptor and Activates Hepatic Adenylate Cyclase" J. Biol. Chem., 1979, 254 (2), 268.
Baird, G.D., "Primary Ketosis in the High–Producing Dairy Cow: Clinical and Subclinical Disorders, Treatment, Prevention, and Outlook" J. Dairy Sci., 1982, 65, 1–10.
Drackley, et al., "Metabolic Responses of Lactating Goats to Feed Restriction and Dietary 1.3–Butanediol." J. Dairy Sci., 1989, 72, 3204.
Bauman, D.E., "Intermediary Metabolism of Adipose Tissue" Fed. Proc., 1976, 35 (11), 2308.
Herdt, T.H., et al., "Hepatic Triacylglycerol Synthesis During a Period of Fatty Liver Development in Sheep" J. Anim. Sci., 1988, 66, 1997–2013.
Gerloff, B.J., et al., "Inositol and Hepatic Lipidosis. Effect of Inositol Supplementation and Time From Partition on Liver and Serum LIpids in Dairy Cows" J. Anim. Sci., 1986, 62, 1682–1692.
Malinovska, V., et al., "The Therapeutic Effect of Glucagon Chelaton III on the Arterial Wall after Experimental Lipidosis and Calcification" Chem. Abst. 1984:35342, 1983.
Brockman, R.P., "Roles for Insulin Glucagon in the Development of Ruminant Ketosis (Review)", Can. Vet. J., 1979, 20, 121.
Brockman, R.P., "Effects of Glucagon and Insulin on Lipolysis and Ketogensis in Sheep" Ca. J. Comp. Med., 1976, 40, 166.

*Primary Examiner*—Cecilia J. Tsang
*Assistant Examiner*—Fabian A. Jameison
*Attorney, Agent, or Firm*—Zarley, McKee, Thomte, Voorhees & Sease

[57] ABSTRACT

The use of glucagon as a metabolic conditioner for dairy cows and other ruminants is described. The glucagon is preferably administered in an amount of from 1–10 mg per day, preferably during the time period beginning 7 days before calving and continuing until 21 days after calving. The administration of glucagon decreases the incidence of metabolic diseases and metabolic imbalances associated with fatty liver, allows cows to reach peak mile production sooner, and results in increased feed intake during the early stages of lactation.

24 Claims, 3 Drawing Sheets

USE OF GLUCAGON AS A METABOLIC CONDITIONER FOR DAIRY COWS AND OTHER RUMINANTS

CROSS-REFERENCE TO A RELATED APPLICATION

This application claims the benefit of U.S. Provisional Application Ser. No. 60/040,647, filed Mar. 6, 1997, the disclosure of which is hereby incorporated by reference.

GRANT REFERENCE CLAUSE

Work for this invention was funded in part by a grant from the United States Department of Agriculture, Agricultural Research Grant #93-03454. The Government may have certain rights in this invention.

FIELD OF THE INVENTION

This invention relates to a composition and method for treating cows and other ruminants with fatty liver. Specifically, this invention relates to a composition and method for preventing the accumulation of lipids or stimulating removal of lipids from the liver in lactating ruminants by using glucagon.

BACKGROUND OF THE INVENTION

The status of liver function in high-producing dairy cows is critical for normal milk production. The liver performs major integrative roles in carbohydrate, protein, and lipid metabolism of dairy cows.

When dairy cows calve and other ruminants give birth, there is consistently an increase in the amount of lipid stored in the liver during the periparturient period. This lipid level increase is commonly known as "fatty liver" or hepatic lipidosis. Normally, this increased lipid deposition causes no obvious health or milk production problems for a cow. However, under particular circumstances, such as depressed feed intake before calving, infection, or metabolic disease, the deposition of lipid in the cow's liver increases further.

Fatty liver is a major metabolic disease which occurs in up to 50% of all dairy cows. Fatty liver is a "hidden", unobservable disorder that is often is diagnosed only after the cow dies from another disease. The costs associated with fatty liver, therefore, are difficult to estimate. However, the costs of clinical and subclinical ketosis, a complication resulting from fatty liver, have been estimated to be at least $300 million yearly.

Fatty liver has been associated with increased susceptibility to other postpartum diseases and decreased fertility. Cows with severe fatty liver retain viable bacteria in the udder for a much longer time (Hill, A. W. et al., "Invluence of liver fat on experimental *Escherichia coli* mastitis in periparturient cows", *Vet. Rec.* 117:549, 1985). Also, cows with fatty livers are leukopenic, with decreases in neutrophils, eosinophils, and lymphocytes (Reid, I. M. et al., "Haematology of sublinical fatty liver in cows", *Res, Vet. Sci.* 37:63, 1984).

Further, fatty liver leads to the development of other serious diseases and disorders that greatly decrease the profitability of dairying. For instance, especially in cows that are somewhat obese at calving, the major accumulation of lipid associated with fatty liver can result in a severe hepatic lipidosis, which can result in decreased feed intake, downer cow syndrome, delayed estrus, and poor conception rates. Moreover, it has been found that fatty liver seems to be a prerequisite for the development of clinical ketosis (Drackley, J. K. et al., "Metabolic changes in dairy cows with ketonemia in response to feed restriction and dietary 1,3-butanediol", *J. Dairy Sci.* 75:1622, 1992). Ketosis is characterized by increased concentration of blood ketone bodies, decreased concentrations of blood glucose, anorexia, and decreased milk production. Further, the above-stated problems become amplified because ruminant livers have little capacity to mobilize lipids, such as triacylglycerols, from liver to other tissues.

The pathology of bovine fatty liver has been described (Collins, R. A. and I. M. Reid, "A correlated biochemical and stereological study of periparturient fatty liver in the dairy cow", *Res. Vet. Sci.*, 28:373, 1980). In severe fatty liver, the accumulation of triacylglycerols (TG) is accompanied by disturbances in hepatic structure, including fatty cysts in liver parenchyma, increased cell volume, compression of sinusoids, decreased volume of rough endoplasmic reticulum, and mitochondrial damage. The latter two changes are reflected by decreased concentrations of albumin and increased activities of mitochondrial enzymes released into the blood.

There is therefore a need in the art for a method to prevent the accumulation of lipids and/or a method to stimulate the removal of lipids from the liver of ruminants after calving.

There are two widely accepted functions of glucagon in mammals. These are: 1) to stimulate glucose synthesis and glycogenolysis in liver in order to increase glucose release into the bloodstream; and 2) to stimulate lipolysis in adipose tissue and thereby release nonesterified fatty acids (NEFA) into the bloodstream. Normally, NEFA released from adipose tissue are oxidized for energy by muscle and other tissues such as liver. However, if blood NEFA become too high, some storage of the NEFA can occur in the liver. While humans are able to remove these fatty acids (i.e. lipids) from the liver, ruminants have almost no capacity to remove lipids from the liver.

Based on this conventional understanding of glucagon function, the present inventors originally hypothesized that the administration of glucagon to ruminants would stimulate lipolysis from adipose tissue in lactating cows, which would greatly increase the possibility of those cows accumulating fat in the liver. Thus, the inventors believed that the administration of exogenous glucagon would actually increase the incidence of fatty liver in dairy cows. Surprisingly, the inventors have discovered that the administration of glucagon to cows after calving at the specified low dosages results in a significantly decreased amount of lipid in livers of high-producing lactating cows. Thus, with respect to lipid metabolism, glucagon acts very differently in cattle than it does in humans and other non-ruminant species.

Accordingly, it is a primary objective of the present invention to provide a composition and method for treating fatty liver in high-producing lactating cows and other ruminants using glucagon.

It is a further objective of the present invention to provide a composition and method for treating fatty liver in high-producing lactating ruminants using glucagon which decreases the incidence of metabolic diseases and metabolic imbalances.

It is a further objective of the present invention to provide a composition and method for treating fatty liver in high-producing lactating ruminants using glucagon which allows cows to reach peak milk production sooner.

It is yet a further objective of the present invention to provide a composition and method for treating fatty liver in high-producing lactating ruminants using glucagon which results in increased feed intake during the first few days of lactation.

It is still a further objective of the present invention to provide a composition and method for treating fatty liver in high-producing lactating ruminants using glucagon which is not harmful to the animal and is relatively inexpensive.

The method and means of accomplishing each of the above objectives as well as others will become apparent from the detailed description of the invention which follows hereafter.

SUMMARY OF THE INVENTION

The invention describes a method and composition for treating fatty liver in high-producing lactating ruminants with glucagon, its prodrugs and analogues. The glucagon is preferably administered via an implant or subcutaneous injection that releases glucagon slowly for 10 to 14 days. The glucagon treatment is administered for the time period beginning from about 7 days before until 21 days after calving.

Glucagon treatment in lactating ruminants decreases the incidence of metabolic diseases and metabolic imbalances associated with fatty liver, allows cows to reach peak milk production sooner, and results in increased feed intake during the first few days of lactation. The method is also not harmful to the animal and is relatively inexpensive.

DETAILED DESCRIPTION OF THE PREFERRED EMBODIMENT

The present invention relates to a new use for glucagon. As used herein the term "glucagon" shall include glucagon, its prodrugs, its analogues, and any other compound with glucagon-like activity as described in Devlin, T. M. (1992), *Textbook of Biochemistry With Clinical Correlations*, 3rd ed., and *Handbook of Experimental Pharmacology* (1996), "Glucagon III" Vol. 23, (edited by P. J. Lefebure and published by Springer, New York), the relevant portions of which are herein incorporated by reference.

The major use of glucagon is for emergency treatment of severe hypoglycemic reactions in insulin-dependent patients when unconsciousness prohibits oral feedings. Glucagon is relatively free of severe adverse reactions with transient nausea and occasional vomiting being the main side effects.

Glucagon is a hormone secreted by the alpha cells of the islets of Langerhans when the blood glucose concentration falls. It has several functions that are diametrically opposed to those of insulin. Most important of these is to raise blood glucose at the expense of stored hepatic glycogen. Glucagon also increases the extraction of amino acids from the blood by the liver cells, thus making a greater quantity of these available to be converted to glucose.

Glucagon is a large polypeptide which is identical in all mammals. It has a molecular weight of 3485 and is composed of a chain of 29 amino acids. Glucagon has the following amino acid sequence:

```
                                          SEQ ID NO:1
H-His-Ser-Gln-Gly-Thr-Phe-Thr-Ser-Asp-Tyr-Ser-Lys-
  1                                               12

Tyr-Leu-Asp-Ser-Arg-Arg-Ala-Gln-Asp-Phe-Val-Gln-
13                                              24

Trp-Leu-Met-Asn-Thr-OH
25                  29
```

Some reports indicate a Glu at position 3 of this sequence either sequence would be operable in the invention. Binding to the receptor triggers the activation of adenylate cyclase to promote an increase in the intracellular concetration of CAMP. The cAMP activates protein kinase that then catalyzes phophorylation of glycogen phosphorylase to promote the release of glucose-1-phosphate from glycogen. Studies show that extracellular glucagon works through binding the glucagon receptor in the cell membrane.

The present invention is predicated upon the discovery that glucagon provides an effective means of treating increased concentrations of lipids in the livers of lactating ruminants. At the beginning of lactation, high-producing dairy cows often have poor appetites, are not producing nearly as much milk as during the previous lactation, are generally lethargic, and sometimes develop "downer cow" syndrome. As a result, the dairy cows usually cannot maintain positive energy balance during early lactation, and this deficit of dietary energy limits milk production. Consequently, dairy farmers often try to fatten cows as much as possible in late lactation and during the early dry period so the cows will have abundant energy reserves to begin the next lactation. Too much fattening, however, causes cows to have major problems adapting to lactation, and they mobilize lipid reserves from adipose tissue at an excessive rate, resulting in accumulation of excessive lipids in the liver.

Administration of glucagon allows cows to become fattened more at the end of one lactation and then to efficiently utilize excess body fat at the beginning of the next lactation to increase production efficiency without greatly affecting the health of the cow.

The administration of glucagon results in increased clearance of triacylglycerols from the liver, thereby decreasing the occurrence of fatty liver. This allows cows to reach peak milk production sooner, and to have an increased feed intake during the early stages of lactation. These effects are associated with the ability of glucagon to increase the concentration of glucose in blood. Ruminants are almost completely dependent on gluconeogenesis for supplying blood glucose and cows usually have decreased concentrations of blood glucose during early lactation. In many areas of the world, buffalo, sheep, and goats are used for milk production, and this same glucagon treatment method is also applicable to these other lactating farm ruminants.

The administration of glucagon to ruminants has several additional benefits. The administration of glucagon just before the time of insemination in cows increases the conception rates in high-producing cows, which often have difficulties in becoming pregnant.

Second, a major problem in the sheep industry is pregnancy toxemia in ewes pregnant with twins or triplets. This metabolic disease is caused when ewes are fed low quality feed or forages and cannot consume enough energy and cannot synthesize enough glucose. This condition usually results in death of the ewe. The administration of glucagon is effective in treating pregnancy toxemia in sheep and also in lactating goats.

Third, the practice of "flushing" or providing extra energy has been used for many years in farm animals such as swine, cattle, and sheep to improve the energy status of animal and to increase conception rates and the number of live offspring born. Administration of glucagon serves the same purpose of augmenting the benefits of flushing by increasing blood glucose and liver glycogen.

Fourth, increasing the glycogen content of meat increases the juiciness (via water-holding capacity) and flavor of meat. Glucagon administration structured to cause increased glycogen in muscle provides many benefits to the meat industry. This is of most value in swine where current breeding and feeding practices combine to give very lean cuts of pork that are often fairly dry and lacking full flavor.

Fifth, glucagon increase the lactose content of milk from cows and such an effect in sows is beneficial in the growth of young pigs.

Further, laying hens sometimes have difficulty with fatty-liver-kidney syndrome. By administrating glucagon, such difficulties in laying hens would be prevented or alleviated.

Moreover, the benefits of glucagon are extendible to humans. Humans with untreated or poorly controlled diabetes often have fatty liver. This fatty liver could be treated through the administration of glucagon.

The administration of glucagon to ruminants has the added benefit of decreasing the incidence of infectious diseases, such as mastitis, which is more predominant in cows with fatty livers. Further, glucagon administration decreases the incidence of retained placenta after calving as well as metritis.

Although not wishing to be bound by any theory, it is believed that the administration of glucagon increases the rate of clearance of the lipid triacylglycerol from the liver. This may occur due to an increase in the rates of assembly and secretion of lipoproteins. This removal of triacylglycerol from the liver markedly decreases the incidence and severity of lactation ketosis.

Treatment of ruminants with exogenous glucagon can also be used very effectively to prevent a detrimental buildup of triacylglycerol in the liver around the time of parturition and to consequently prevent most cases of clinical ketosis in high-producing dairy cows.

Glucagon is currently available in parenteral dosage forms for intramuscular, intravenous, or subcutaneous administration. Glucagon is typically reconstituted in a sterile water carrier for a final dosage in the range of from 0.25 to 1.0 mg. For purposes of this invention as applied to dairy cows and buffalo, the glucagon is given in dosages of from about 1–10 mg/day. The preferred dose is from about 5–10 mg/day, with the most preferred dose being about 10 mg/day.

With respect to sheep and goats, the dose of glucagon given should be about 1/10–2/10 of the amounts in the preceding paragraph given to dairy cows and buffalo.

Even lower concentrations of glucagon in the carrier will be suitable, requiring only that more frequent administration be resorted to. As a practical matter, however, to avoid the need for repeated administration, it is desirable that the glucagon preparation be formulated to release from 1–10 mg of glucagon. Similarly, it may not be any more worthwhile to the animal to administer doses of glucagon greater than 10 mg/day. In fact, the inventors' preliminary data indicate that doses of greater than 10 mg/day may actually increase the incidence of fatty liver in early lactation dairy cows.

The glucagon can be given to the ruminant for a time period up to 35 days post partum. The glucagon is preferably given to the ruminant during the period beginning around 7 days before and continuing until 21 days after calving, since this is the time period when fatty liver tends to develop. The glucagon is still beneficial to the animal if given for shorter periods during this time frame. For practical reasons, the glucagon is not administered for longer periods of time since, while not harmful, there may not be any additional benefit to the animal. For convenience, a preferred form of administration is via a controlled release glucagon implant or a subcutaneous injection.

It is understood that the present invention contemplates the use of not only glucagon itself, but its prodrugs, which metabolize to the compound and the analogues and biologically active salt forms thereof, as well as optical isomers and glucagon-like peptides which provide the same pharmaceutical results as glucagon. Since it is the first six amino acids at the N-terminus of the glucagon molecule which bind to specific receptors on liver cells, these amino acids must be conserved. Information relating to glucagon prodrugs and analogues is set forth in Devlin, T. M. (1992), *Textbook of Biochemistry With Clinical Correlations*, 3rd ed., and *Handbook of Experimental Pharmacology* (1996), "Glucagon III" Vol. 23, (edited by P. J. Lefebure and published by Springer, New York), the relevant portions of which are herein incorporated by reference.

The glucagon preparations can include a variety of substances including, but not limited to, preservatives, dyes, fillers, vitamins, minerals, and amino acids. These minors are added in small amounts and are conventionally known in pharmaceutical formulation work to enhance elegance. Such minors should comprise less than 1% of the overall composition.

Other drugs or nutrients may also be added to the glucagon composition, so long as it is compatible with glucagon and the remaining ingredients. For instance, if the cow had a bacterial infection, the glucagon preparation could include an antibiotic.

The most publicized agent in recent years for dairy production and management has been bovine somatotrophin (BST). Implants of that hormone have been shown to increase milk production and milk production efficiency. However, BST is not indicated for administration until at least 9 weeks into lactation and after cows are settled into a stable energy balance and steady milk production. In contrast, glucagon is administered several weeks prior to the time when BST can be given. The glucagon and BST can therefore be utilized hand-in-hand to increase milk production efficiency in cows to obtain an increased and earlier response in comparison to BST used alone.

While glucagon is conventionally formulated in a parenteral form, it is contemplated that it can also be contained in a variety of other dosage forms. In general, in addition to the glucagon, the pharmaceutical compositions of this invention may contain suitable excipients and auxiliaries which facilitate processing of the active compounds into preparations which can be used pharmaceutically. Oral dosage forms encompass tablets, dragees, capsules, and feed supplements. Preparations which can be administered rectally include suppositories. Other dosage forms include suitable solutions for administration parenterally, orally, or nasally, and compositions which can be administered buccally or sublingually.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include for example liquid triglycerides, polyethylene glycols, or paraffin hydrocarbons.

Suitable formulations for parenteral, subcutaneous, and intramuscular administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension including, for example, sodium carboxymethyl cellulose, sorbitol and/or dextran. Optionally, the suspension may also contain stabilizers.

In addition to administration with conventional carriers, active ingredients may be administered by a variety of specialized delivery drug techniques which are known to those of skill in the art, such as portable infusion pumps.

The following examples are offered to illustrate but not limit the invention. Thus, they are presented with the understanding that various formulation modifications as well as method of delivery modifications may be made and still be within the spirit of the invention.

EXAMPLE

EFFECT OF GLUCAGON ON LIVER TRIACYLGLYCEROL LEVELS OF DAIRY COWS

Materials and Methods

Glucagon purified from bovine pancreas, was weighed, dissolved in 0.09% NaCl adjusted to pH 10.5, and diluted so that the amount to be infused daily was contained in 480 ml to allow for an infusion rate of 20 ml/h. All glassware that was to be in contact with glucagon was rinsed with a solution of 1.0% bovine serum albumin to prevent adherence of glucagon to glass surfaces.

The four groups of 10 multiparous Holstein cows per group that were used for the main trial were normal controls (NC), normal cows treated with glucagon (NTG), susceptible controls that should be inducible into ketosis (SC), and susceptible cows treated with glucagon (STG). The two groups of 10 normal cows were selected from cows that had body condition scores at calving that ranged from 3.2 to 3.8. The two groups of 10 susceptible cows were selected from obese cows that have been fed at 2 times NRC requirements for energy during late lactation and throughout the dry period so they calved at a body condition score of 4.0 to 4.5. Based upon an earlier trial, a relationship between liver triacylglycerol:glycogen (TG:GY) ratio and body condition at calving was found. Previous data suggested that cows in early lactation with liver TG:GY somewhere below 2 are resistant to fatty liver and ketosis when challenged with the FRBD protocol.

A liver biopsy was taken at 7 days postpartum and analyzed immediately for triacylglycerols and glycogen. Normal cows having a liver TG:GY ratio less than 2.0 or TG less than 5% (wet weight basis) were assigned alternately to the NC and the NTG groups. A high percentage (i.e.>90%) of these cows should be resistant to ketosis, as is the case for cows in most dairy herds. Susceptible cows having a liver TG:GY greater that 2.5 were assigned alternately to the SC and STG groups.

On d 14 postpartum, the SC and the STG groups began the FRBD (feed restriction and 1,3-butanediol in the diet) protocol in which feed intake was restricted to 80% of the average intake for the previous 2 days and 1,3-butanediol (BD) was added, a precursor of ketone bodies, to the ration in increasing quantities either until the cow became ketotic or until 1.4 kg of BD was offered daily. The STG group at 21 days postpartum began to receive a continuous intravenous infusion of 10 mg of glucagon daily, which continued for 14 days. The SC group were infused with saline as a vehicle control. The NC and the NTG groups continued to receive feed for ad libitum intake, but the NTG group received an infusion of glucagon from d 21 to 35 postpartum and the NC group was infused with vehicle control. (The NTG group gave information on how normal early lactation cows respond to 14-day intravenous infusions of glucagon).

The objectives of the project involved the same measurements being made on all four groups of cows (NC, NTG, SC, and STG). Therefore, the description of procedures is divided into obtaining liver samples, analyses on liver samples, analyses on blood samples, and analyses on mild samples.

obtaining Liver Samples

Liver samples were taken by puncture biopsy on days 7, 13, 20, 23, 27, 35, 38, 41, and 49. Each biopsy sample usually weighed 3 to 5 g, and normally two samples could be obtained without danger to the cow at each collection. Liver biopsies have been routinely obtained from biopsies without evidence of significant damage to the cows. For some cows, there was a small decrease in feed intake and milk production for 12 hours after biopsy.

Biopsies to obtain samples of liver were according to the following schedule and rationale:

| Day postpartum | Treatment of cows or rationale for biopsying |
|---|---|
| 6 | This early postpartum sample was taken and analyzed for glycerol, triacylglycerol, and total lipid within 24 h. The TG:GY ratios was the criteria for assignment of cows to the normal or susceptible groups. |
| 13 | This second sample provided information on liver composition the day before the FRBD protocol began for both susceptible groups, and it also served to satisfy criteria for assignment to treatments if the d-6 liver biopsy was borderline. |
| 20 | FRBD had been underway for 5 d, and glucagon infusions were to begin for the NTG and STG groups within a day. |
| 23 | These liver samples, taken 2 d after glucagon infusions began, were to identify immediate changes occurring during the first 2 d of glucagon infusion. |
| 27 | These liver samples, taken 5 days after glucagon infusions began, were to identify changes in liver composition during those 5 days. |
| 35 | The full extent of changes caused by glucagon were revealed by samples taken just after the glucagon infusions were terminated. The biopsies were taken within 2 h after glucagon infusions were terminated for the NTG and STG groups. |
| 38 | This sample, taken 3 d after the glucagon infusions were stopped, showed short-term adjustments in the liver of STG cows and NTG cows caused by terminating the glucagon treatment. |
| 41 | Samples of liver taken 7 d after the glucagon infusions were stopped gave information on changes in liver composition following termination of glucagon infusion, and they were also at the end of the FRBD protocol. |
| 49 | Samples taken 2 wk after the glucagon infusions were stopped and 1 wk after FRBD was stopped revealed how the liver had adjusted. |

Analyses on Liver Samples

As soon as a "plug" of liver was removed by the biopsy cannula, it was placed on absorbent paper and blotted free of blood. Then, the sample of liver was frozen immediately by dropping into liquid nitrogen and eventually used for assay of concentrations of glycogen, triacylglycerol, total lipids, and PEPCK mRNA. (PEPCK is a major enzyme controlling gluconeogenesis, and measurement of amounts of its mRNA provided information on controls of gluconeogenesis in the groups of cows).

Glycogen and triacylglycerol concentrations of liver samples were determined as described by Mills, S. E. et al., "Characterization of metabolic changes during a protocol for inducing lactation ketosis in dairy cows", *J. Dairy Sci.* 69:352 (1986a). Total lipid content was measured as described by Drackley, J. K. et al., "Metabolic changes in blood and liver of dairy cows during feed restriction or administration of 1,3-butanediol", *J. Dairy Sci.*, 74:4254 (1991). Potential changes in gluconeogenic capacity also was estimated by measuring the amount of PEPCK mRNA by Northern blotting (Maniatis et al., Molecular Cloning, 2nd ed., 1988).

Analyses on Blood Samples

Blood samples were taken daily from d 7 through 49 and d 21 and 35. "Window" samples were taken every 30 minutes for 7 hours as the glucagon infusions were begun and terminated, respectively. Blood plasma was analyzed for concentrations of glucose (Sigma, glucose oxidase), non-esterified fatty acids (Shimizu, S. K. et al., "Enzymatic microdetermination of serum free fatty acids", *Anal. Biochem.*, 98:341, 1979), 3-hydroxybutyrate (Williamson, D. H. and J. Mellanby, D-(−)-3-hydroxybutyrate, Page 1836 in H. U. Bergmeyer, ed. "Methods of enzymatic analysis" Vol. 3, 2nd ed. Academic Press, New York, N.Y. 1974), and acetoacetate (Mellanby and Williamson, Page 1836 in H. U. Bergmeyer, ed. "Methods of enzymatic analysis" Vol. 3, 2nd ed. Academic Press, London, 1974). Concentrations of glucagon (Herbein et al., 1985) and insulin (Elsasser et al., 1986) were assayed in samples of blood plasma taken. Jugular vein catheters were established one day before blood samples were taken for the window samplings to avoid unnecessary stress during the samplings.

Analyses of Milk Samples

Weight of milk was recorded at every milking, and any health problem or unusual occurrence was recorded also. Samples of milk were taken at least weekly and more often at strategic times (i.e., 20, 221, 22, and 34, 35, 36 d). Content of fat, protein, and lactose in the mild samples was determined (Milk-O-Scan 203, Foss Food Technology, Eden Prairie, Minn.).

Analysis and Interpretation of Data

The experiment was a 2×2 factorial with two nutritional backgrounds (normal and susceptible) and two levels of glucagon infusion (0 and 10 mg/day). There were four treatment groups within the experiment: NC, NTG, SC, and STG. The multiple samplings of liver, blood, and milk made the experiment a split-plot design in time, with days postpartum for sampling being the sub-plots. Statistical analyses were done by using SAS in consultation with Dr. D. F. Cox, a long-time consulting statistician for Iowa State University.

Extensive results were obtained from analyses of blood and liver with respect to metabolites and changes in hepatic lipid deposition. It was calculated that 10 cows per treatment would allow detection of significant differences as small as 10% for the items measured.

Results

Figure 1:
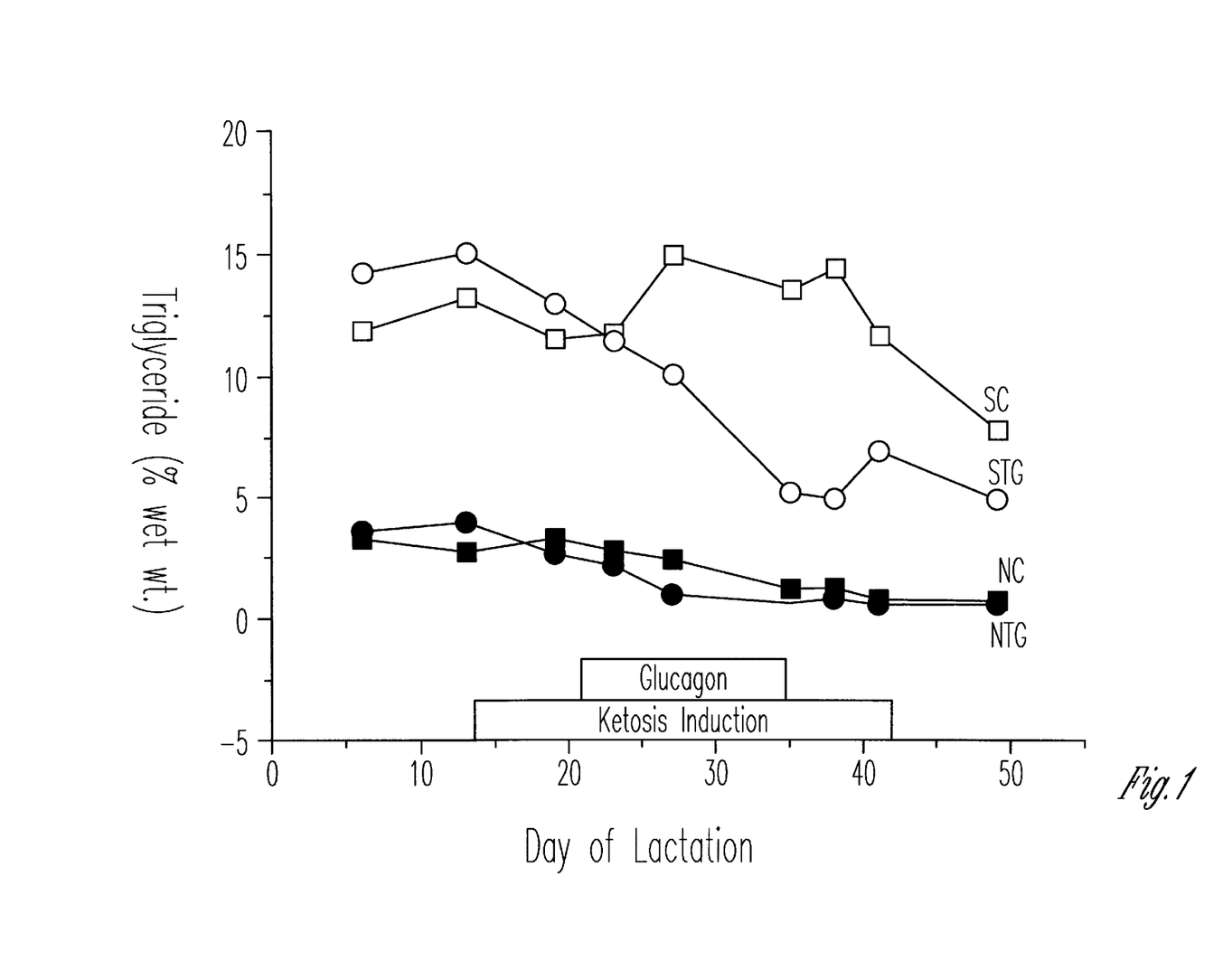
FIG. 1 is a graph showing the liver triacylglycerol treatment averages on days 14–42 of lactation in four groups of cows: controls that are susceptible to ketosis (SC), ketosis susceptible controls treated with glucagon (STG), normal controls (NC), and normal cows treated with glucagon (NTG).

Four groups of 10 cows were used in the study to determine the effect of the administration of glycogen on the liver triacylglycerol levels of dairy cows (see FIG. 1). The first group (SC) comprised susceptible controls (SC) that were created by major overfeeding throughout the dry period so that they were obese at calving. After calving, they were managed and fed as normal herd cows for the first 14 days. Liver biopsies were taken beginning at 7 days after calving and analyzed for triacylglycerol (fat) and glycogen (carbohydrate). The fact that this group of cows had 12 to 13% fat in the liver at those times indicated they probably were susceptible to ketosis. Susceptibility was challenged by an induction protocol that was given from d 14 through d 42 postpartum. All of these cows became clinically ketotic and the amount of fat in the liver continued to be high.

The second group was susceptible cows given the ketosis induction protocol as for the SC group but also treated with glucagon (STG) at 10 mg/d for 14 days. The major difference in response was that glucagon caused removal of lipids from the livers of the STG group so that the lipid percentage had decreased to only 5 to 6% at the end of the glucagon infusions. Previous results have shown that cows with less than 5% lipid in the liver are very difficult or impossible to induce into ketosis. Therefore, if cows were treated with glucagon before calving or within 3 days after calving that these cows would not accumulate amounts of lipid in the liver that are above normal and that these cows would be highly resistant to ketosis.

The third and fourth groups of cows were normal controls (NC) that were fed and managed during the dry period according to NRC recommendations and normal cows treated with glucagon (NTG). FIG. 1 shows that these cows did not have greatly elevated concentrations of lipid in their livers at 7 days postpartum. Therefore, treatment with glucagon caused no major decrease in the concentration of lipid in livers of normal cows.

Figure 2:
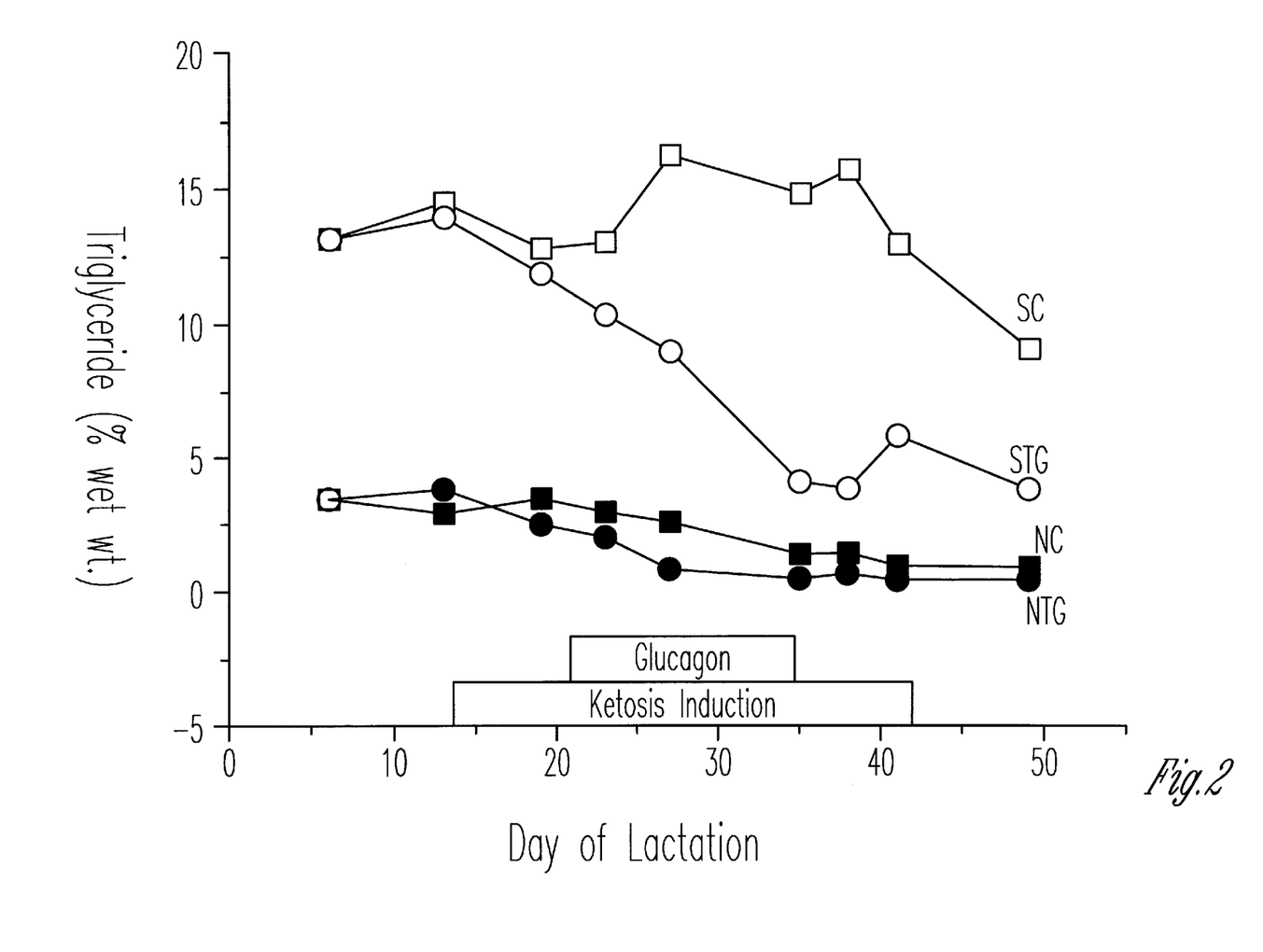
FIG. 2 is a graph representing the same data as in FIG. 1, except that the data for all four cow types were covariate adjusted to the average day 7 value combined.

FIG. 2 presents the same data as in FIG. 1, except that the data for all cows were covariate adjusted to the average d-7 value combined both groups of susceptible and normal cows for fat content of the livers. Clearly, the covariate adjustment shows the effects of glucagon on the triacylglycerol concentration of the liver in susceptible cows even more dramatically. Again, there was only a slight difference between the NC and the NTG groups.

Figure 3:
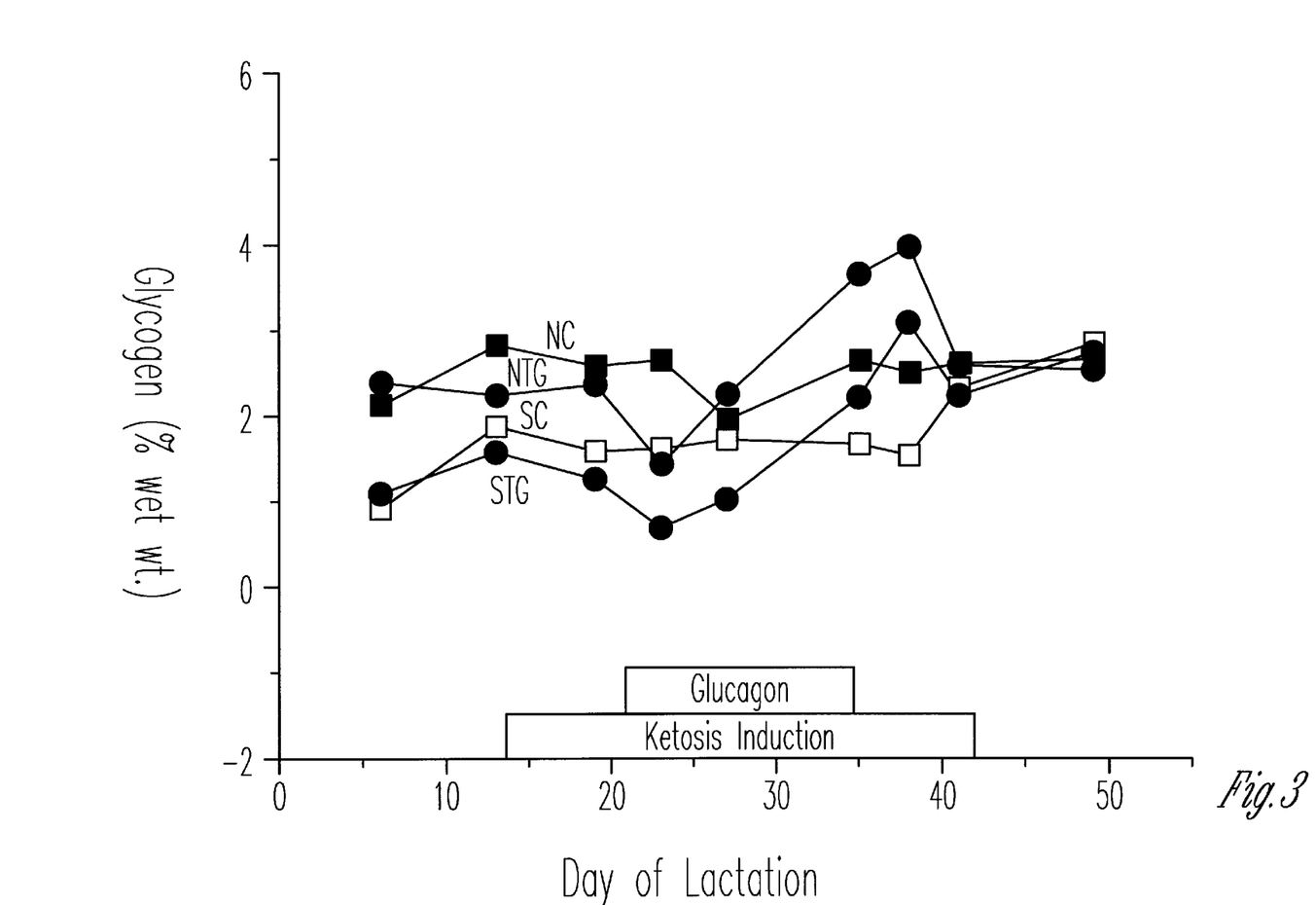
FIG. 3 is a graph showing the liver glycogen treatment averages for the four cow groups SC, STG, NC, and NTG on days 14–42 of lactation.

FIG. 3 shows the glycogen contents for the four groups. First, the normal groups had higher concentrations of glycogen in the liver at d 7 postpartum than did the susceptible groups. This result was expected. Second, when glucagon infusions began in the NTG and STG groups at d 21, concentrations of liver glycogen decreased from the 20-d biopsy sample to the 23-d sample. This effect was caused by glycogenolysis. Third, glycogen concentrations in both the NTG and STG groups increased at a parallel rate from d 23 up to the biopsy taken at d 38, which was 3 d after glucagon infusions were stopped. Fourth, glycogen content dropped dramatically before the 42-d biopsy, and glycogen levels for all four groups were essentially the same at 42 and 49 of lactation. During the entire 49-day span, glycogen concentrations remained relatively constant for the NC group, whereas it gradually drifted upward for the SC group.

The essence of these results is that glucagon has the ability to promote removal of triacylglycerol from the liver and also the ability to prevent the accumulation of triacylglycerol in the liver. And it can also increase the glycogen content of liver. The decrease in liver triacylglycerol, prevention of triacylglycerol accumulation in the liver, and the increase in liver glycogen are beneficial changes to the health and well-being of high-producing dairy cows.

As shown above, the treatment of dairy cows and other ruminants with glucagon decreases the incidence of metabolic diseases and metabolic imbalances associated with fatty liver, allows ruminants to reach peak milk production sooner, and results in increased feed intake during the early stages of lactation. These effects take place without any indication of glucagon toxicity in the animals.

It should be appreciated that the glucagon treatment may contain glucagon, or prodrugs or analogues of glucagon or a racemic mixture including (where applicable) either the D or the L form. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A composition for increasing the rate of clearance of triacylglycerol from the liver in dairy cows and other ruminants comprising:

glucagon; and a pharmaceutically acceptable carrier;

wherein the amount of glucagon in the composition is an effective amount formulated to release 1–10 mg of glucagon or an equivalent effective amount of a glucagon prodrug or analogue;

and further providing that the composition is formulated into a parental dosage form.

2. A composition according to claim 1 wherein the pharmaceutically acceptable carrier is aqueous.

3. A composition according to claim 1 which contains from about 5–10 mg of glucagon per day.

4. A composition according to claim 3 which contains about 10 mg of glucagon.

5. A composition according to claim 1 which is formulated into a sustained release parenteral dosage form.

6. A composition according to claim 5 wherein the sustained release parenteral dosage form releases the glucagon gradually over a time period of 10–14 days.

7. A composition according to claim 6 wherein the glucagon is administered via a form selected from the group consisting of an implant, an injectable for subcutaneous injection, and an injectable for intramuscular injection.

8. A composition according to claim 1 wherein the composition further includes a suitable pharmaceutical excipient selected from the group consisting of fillers, lubricants, binders, colorings, and flavorings.

9. A method of increasing the rate of clearance of triacylglycerol from the liver in dairy cows and other ruminants comprising:

administrating glucagon or to the ruminant;

a glucagon analogue, prodrug which includes the first six amino acids at the N-terminus of SEQ ID NO:1; and a pharmaceutically acceptable carrier;

wherein the amount of glucagon in the composition is formulated to release 1–10 mg of glucagon or an equivalent effective amount of said analogue, or prodrug.

10. A method according to claim 9 wherein the glucagon is administered in a dose of from about 1–10 mg/day.

11. A method according to claim 10 wherein the glucagon is administered to the ruminant for a time period of about 14 days post partum.

12. A method according to claim 11 wherein the glucagon is administered to the ruminant between 7 days before and 21 days after calving.

13. A method according to claim 10 wherein the glucagon is administered using a method selected from the group consisting of parenterally, orally, intranasally, and rectally.

14. A method according to claim 13 wherein the glucagon is administered via a route selected from the group consisting of an implant, a subcutaneous injection, and an intramuscular injection.

15. A method according to claim 14 wherein the glucagon is administered to the ruminant in a dosage form which releases the glucagon slowly over a time period of 10–14 days.

16. A method according to claim 13 wherein the glucagon is administered orally by adding it to the ruminants' feed.

17. A method according to claim 13 wherein the glucagon is administered to a dairy cow.

18. A method of preparing a glucagon composition for use as a treatment for hepatic lipidosis in ruminants comprising:

combining a hepatic lipidosis treatment effective amount of glucagon with a pharmaceutically acceptable carrier.

19. A method according to claim 18 wherein the glucagon composition is placed in a dosage form selected from the group consisting of oral, parenteral, rectal, and intranasal.

20. A method according to claim 19 wherein the glucagon composition is placed in a dosage form for parenteral administration which is designed to release the glucagon slowly over a time period of 10–14 days.

21. A composition for use as a metabolic conditioner for dairy cows and other ruminants comprising:

the first six amino acids at the N-terminus of the glucagon molecule; and a pharmaceutically acceptable carrier.

22. A method of increasing the rate of clearance of triacylglycerol from the liver in dairy cows and other ruminants comprising:

administering a glucagon analogue, or prodrug which includes the first six amino acids at the N-terminus of SEQ ID NO:1 to the ruminant.

23. A method of treating hepatic lipidosis in dairy cows comprising:

administrating glucagon, a glucagon analogue, or prodrug on the cow.

24. A method of increasing the rate of clearance of triacylglycerol from the liver in dairy cows and other ruminants comprising:

administrating glucagon to the ruminant between 7 days before and 28 days after calving.

\* \* \* \* \*

SEQUENCE LISTING

<160> NUMBER OF SEQ ID NOS: 1

<210> SEQ ID NO 1
<211> LENGTH: 29
<212> TYPE: PRT
<213> ORGANISM: mammalian

<400> SEQUENCE: 1

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr
            20                  25